(12) United States Patent
Ito et al.

(10) Patent No.: US 10,330,752 B2
(45) Date of Patent: Jun. 25, 2019

(54) MAGNETIC RESONANCE IMAGING APPARATUS AND METHOD FOR SETTING RF SHIMMING PARAMETERS

(71) Applicant: HITACHI, LTD., Tokyo (JP)

(72) Inventors: Kosuke Ito, Tokyo (JP); Yoshihisa Soutome, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 54 days.

(21) Appl. No.: 15/547,535

(22) PCT Filed: Feb. 15, 2016

(86) PCT No.: PCT/JP2016/054226
§ 371 (c)(1),
(2) Date: Jul. 31, 2017

(87) PCT Pub. No.: WO2016/143460
PCT Pub. Date: Sep. 15, 2016

(65) Prior Publication Data
US 2018/0011155 A1    Jan. 11, 2018

(30) Foreign Application Priority Data
Mar. 6, 2015  (JP) ................................ 2015-044912

(51) Int. Cl.
*G01R 33/36* (2006.01)
*A61B 5/055* (2006.01)
(Continued)

(52) U.S. Cl.
CPC .......... *G01R 33/3607* (2013.01); *A61B 5/055* (2013.01); *G01R 33/288* (2013.01); *G01R 33/5659* (2013.01); *G01R 33/246* (2013.01)

(58) Field of Classification Search
CPC ............ G01R 33/3607; G01R 33/5659; G01R 33/288; G01R 33/246; A61B 5/055
See application file for complete search history.

(56) References Cited

U.S. PATENT DOCUMENTS

| 2009/0322330 A1 | 12/2009 | Adachi et al. |
| 2013/0082708 A1* | 4/2013 | Yokosawa ............... A61B 5/055 324/309 |

(Continued)

FOREIGN PATENT DOCUMENTS

| JP | 2014-23961 | 2/2014 |
| JP | 2014-236868 | 12/2014 |
| WO | WO2014/021172 A1 | 2/2014 |

OTHER PUBLICATIONS

International Search Report dated May 17, 2016 in connection with PCT/JP2016/054226.

*Primary Examiner* — Tung X Nguyen
*Assistant Examiner* — Dominic E Hawkins
(74) *Attorney, Agent, or Firm* — Cooper & Dunham LLP (57) ABSTRACT

In order to improve B1 non-homogeneity while reducing a local SAR in an object, particularly, in a human tissue during MR imaging, the present invention is characterized in that each of a plurality of irradiation channels is controlled on the basis of RF shimming parameters corresponding to the plurality of irradiation channels, and, in a case of performing imaging sequence of irradiating an object with an RF magnetic field, there is the use of the RF shimming parameters obtained by imposing a constraint condition on at least one of a plurality of principal components obtained through principal component analysis on the RF shimming parameters.

4 Claims, 6 Drawing Sheets

(51) Int. Cl.
*G01R 33/28* (2006.01)
*G01R 33/565* (2006.01)
*G01R 33/24* (2006.01)

(56) References Cited

U.S. PATENT DOCUMENTS

| | | | | |
|---|---|---|---|---|
| 2013/0342207 A1* | 12/2013 | Keupp | ............... | G01R 33/3614 |
| | | | | 324/309 |
| 2014/0070805 A1* | 3/2014 | Van Der Meulen | ......................... | |
| | | | | G01R 33/246 |
| | | | | 324/309 |
| 2014/0292334 A1* | 10/2014 | Kaneko | ................. | A61B 5/055 |
| | | | | 324/309 |
| 2015/0002149 A1* | 1/2015 | Nehrke | ................ | G01R 33/243 |
| | | | | 324/309 |
| 2015/0006114 A1* | 1/2015 | Altbach | ................. | A61B 5/055 |
| | | | | 702/189 |
| 2015/0241539 A1 | 8/2015 | Kaneko et al. | | |
| 2016/0310761 A1* | 10/2016 | Li | ........................ | A61N 5/1038 |

* cited by examiner

MAGNETIC RESONANCE IMAGING APPARATUS AND METHOD FOR SETTING RF SHIMMING PARAMETERS

TECHNICAL FIELD

The present invention relates to a magnetic resonance imaging apparatus and a method for setting RF shimming parameters, and particularly to a technique of improving the homogeneity of a high frequency magnetic field distribution while reducing an electromagnetic wave absorption amount in living body tissue.

BACKGROUND ART

A magnetic resonance imaging (hereinafter, referred to as "MRI") apparatus is an apparatus which measures a nuclear magnetic resonance (hereinafter, referred to as "NMR") signal generated by atomic nucleus spins forming an object, especially, tissues of a human body, and generates morphologies or functions of the head, the abdomen, the limbs and the like of the human body as two-dimensional or three-dimensional images on the basis of a nuclear density distribution, a relaxation time distribution or the like.

In MR imaging, an NMR signal is added with different phase encodes and frequency encodes due to a gradient magnetic field, and is measured as time-series data. The measured NMR signal is subjected to two-dimensional or three-dimensional Fourier transform so as to be reconstructed as an image.

In a high magnetic field MRI apparatus, a resonance frequency of proton is high, and thus a wavelength of a high frequency (hereinafter, referred to as "RF") pulse which is applied to an object is shortened. Thus, a spatial distribution (B1 distribution) of an irradiation RF pulse is non-homogeneous, and thus a problem such as shading or a reduction in an SNR occurs. If a frequency of the irradiation RF pulse is high, an SAR indicating an absorption amount of the RF pulse absorbed by a living body tissue of an object is also high.

As a method of improving the B1 non-homogeneity, there is RF shimming disclosed in PTL 1. The RF shimming method is a technique in which shimming parameters having different amplitude ratios and phase differences are respectively set for a plurality of channels of RF irradiation coils (hereinafter, referred to as irradiation channels), and a spatial distribution of an irradiation RF pulse is made homogeneous.

CITATION LIST

Patent Literature

PTL 1: International Publication No. 2014/021172

SUMMARY OF INVENTION

Technical Problem

However, in RF shimming disclosed in PTL 1 or the like, it is not taken into consideration that a case where a local SAR is heightened depending on a selectable amplitude ratio or a phase difference is excluded.

An object of the present invention is to improve B1 non-homogeneity while reducing a local SAR.

Solution to Problem

In order to achieve the object, the present invention is characterized in that each of a plurality of irradiation channels is controlled on the basis of RF shimming parameters corresponding to the plurality of irradiation channels, and, in a case of performing imaging sequence of irradiating an object with an RF magnetic field, there is the use of the RF shimming parameters obtained by imposing a constraint condition on at least one of a plurality of principal components obtained through principal component analysis on the RF shimming parameters.

Advantageous Effects of Invention

According to the present invention, it is possible to improve B1 non-homogeneity while reducing a local SAR.

DESCRIPTION OF EMBODIMENTS

Hereinafter, a description will be made of an MRI apparatus and a method for setting RF shimming parameters according to the invention on the basis of one embodiment.

Figure 1:
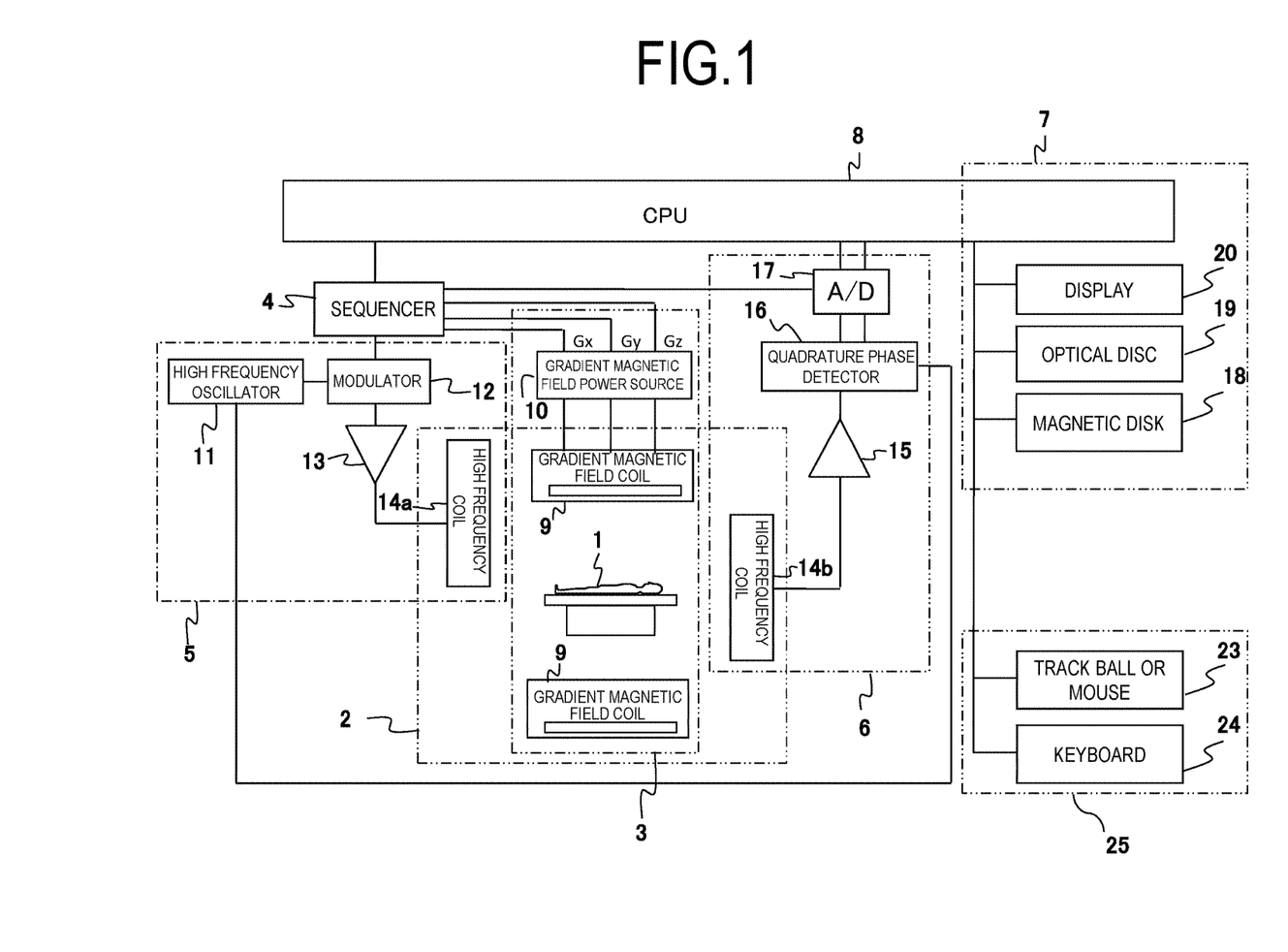
FIG. 1 is the overall configuration diagram of an MRI apparatus according to one Example according to the present invention.

FIG. 1 is the overall configuration diagram illustrating the MRI apparatus according to an embodiment of the present invention. As illustrated, the MRI apparatus is configured to include a static magnetic field generation system 2, a gradient magnetic field generation system 3, a signal transmission system 5, a signal reception system 6, a signal processing system 7, a sequencer 4, and a central processing unit (CPU) 8. The static magnetic field generation system 2 generates a uniform static magnetic field in a space around an object 1 in a direction orthogonal to a body axis of the object in a vertical magnetic field type, and generates a uniform static magnetic field in a body axis direction in a horizontal magnetic field type, and includes a permanent magnet type, normal conducting type, or superconducting type static magnetic field generation source disposed around the object 1.

The gradient magnetic field generation system 3 includes gradient magnetic field coils 9 which are wound in three-axis directions of X, Y, and Z in a coordinate system (static coordinate system) of the MRI apparatus, and a gradient magnetic field power source 10 which drives the gradient magnetic field coils, and applies gradient magnetic fields Gx, Gy and Gz in the three-axis directions of X, Y, and Z by driving the gradient magnetic field power source 10 of each coil in response to a command from the sequencer 4. During imaging, for example, a slice surface is set for the object 1 by applying a slice direction gradient magnetic field pulse (Gs) in a direction which is orthogonal to the slice surface (imaging section), and echo signals are encoded with position information in respective directions by applying a phase encode direction gradient magnetic field pulse (Gp) and a frequency encode direction gradient magnetic field pulse (Gf) in two remaining directions which are orthogonal to the slice surface and are orthogonal to each other.

The sequencer 4 is control means for repeatedly applying a high frequency magnetic field pulse (hereinafter, referred to as an "RF pulse") and the above-described gradient magnetic field pulse according to a predetermined pulse sequence, and is operated under the control of the CPU 8 so as to send various commands which are required to collect data of an MR image which is a tomographic image of the object 1, to the signal transmission system 5, the gradient magnetic field generation system 3, and the signal reception system 6.

The signal transmission system 5 irradiates the object 1 with an RF pulse in order to cause nuclear magnetic resonance in an atomic nucleus spin of an atom forming a living body tissue of the object 1. The signal transmission system 5 includes a high frequency oscillator 11, a modulator 12, a high frequency amplifier 13, and a high frequency coil (signal transmission coil) 14a on the signal transmission side. The modulator 12 amplitude-modulates an RF pulse which is output from the high frequency oscillator 11, at a timing based on a command from the sequencer 4. The amplitude-modulated RF pulse is amplified by the high frequency amplifier 13, then supplied to the high frequency coil 14a disposed near the object 1, and thus the object 1 is irradiated with the RF pulse.

The signal reception system 6 detects an echo signal (NMR signal) emitted due to nuclear magnetic resonance of atomic nucleus spins forming a living body tissue of the object 1, and includes a high frequency coil (signal reception coil) 14b on the signal reception side, a signal amplifier 15, a quadrature phase detector 16, and an A/D converter 17. A responsive NMR signal of the object 1 caused by an electromagnetic wave applied from the high frequency coil 14a on the signal transmission side is detected by the high frequency coil 14b disposed near the object 1. The detected NMR signal which is amplified by the signal amplifier 15 is divided into signals of two systems by the quadrature phase detector 16 at a timing based on a command from the sequencer 4, and the signals are converted into digital signals by the A/D converter 17 so as to be sent to the signal processing system 7.

The signal processing system 7 performs processing of various pieces of data, and display and preservation of a process result, and includes external storage devices such as an optical disc 19 and a magnetic disk 18, and a display 20 formed of a CRT or the like. If data is input to the CPU 8 from the signal reception system 6, the CPU 8 performs processes such as signal processing and image reconstruction, displays an MR image of the object 1 as a result thereof on the display 20, and also records the MR image on the magnetic disk 18 or the like of the external storage device.

An operation unit 25 is used to input various pieces of control information for the MRI apparatus, or control information for processes performed by the signal processing system 7, and includes a track ball or mouse 23, and a keyboard 24. The operation unit 25 is disposed near the display 20, and an operator controls various processes in the MRI apparatus in an interactive manner via the operation unit 25 while viewing the display 20.

In FIG. 1, the high frequency coil 14a on the signal transmission side and the gradient magnetic field coils 9 are provided to oppose the object 1 in a vertical magnetic field type, and to surround the object 1 in a horizontal magnetic field type, in a static magnetic field space of the static magnetic field generation system 2 into which the object 1 is inserted. The high frequency coil 14b on the signal reception side is provided to oppose or surround the object 1.

Currently, an imaging target nuclide of the MRI apparatus, which is clinically popular, is a hydrogen nucleus (proton) which is a main constituent substance of an object. Information regarding a spatial distribution of the proton density or information regarding a spatial distribution of the relaxation time of an excitation state is generated as an image so that a morphology or a function of the human head, abdomen, limbs, or the like is imaged in a two-dimensional or three-dimensional manner.

Here, a description will be made of process procedures of determining RF shimming parameters corresponding to a characteristic technique of the present invention. This process may be performed through cooperation between the signal processing system 7 and the CPU 8, or may be performed by only the CPU 8. Particularly, the present invention is characterized in that a constraint condition is imposed on RF shimming parameters in order to improve B1 non-homogeneity while reducing a local SAR.

An RF shimming parameter of each RF irradiation channel for performing irradiation on a new object is determined on the basis of the RF shimming parameters on which the constraint condition is imposed. Specifically, a plurality of irradiation channels are respectively controlled on the basis of RF shimming parameters corresponding to the plurality of irradiation channels, and, in a case where imaging sequence of irradiating an object with an RF magnetic field is performed, there is the use of an RF shimming parameter obtained by imposing a constraint condition on at least one of a plurality of principal components which are obtained through principal component analysis on RF shimming parameters.

For example, a constraint condition is set according to a contribution ratio of a plurality of principal components to RF shimming parameters of a plurality of irradiation channels. Consequently, a local SAR is reduced, and B1 non-homogeneity is also improved.

Hereinafter, a process of imposing a constraint condition on RF shimming parameters will be described separately in Examples.

Example 1

Figure 2:
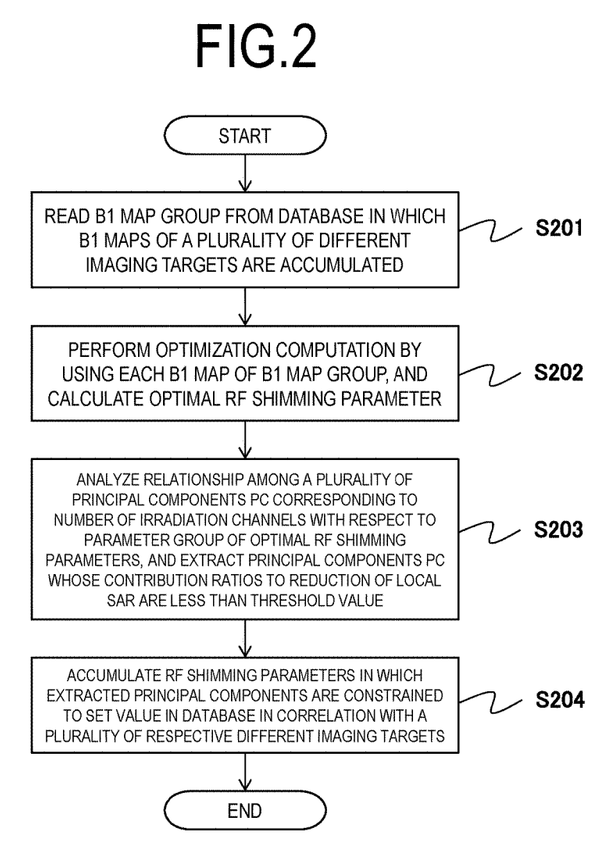
FIG. 2 is a flowchart illustrating procedures of obtaining constraint conditions of RF shimming parameters for reducing an SAR of the MRI apparatus according to the present invention.

FIG. 2 is a flowchart illustrating procedures of a method for setting RF shimming parameters on which a constraint condition is imposed in Example 1. Here, it will be described that B1 non-homogeneity can be improved while reducing a local SAR is reduced by imposing a constraint condition on RF shimming parameters. First, the present inventors of the present invention have found that an optimal RF shimming parameter may be obtained according to RF shimming of the related art, but there is a case where a local SAR is high depending on an amplitude ratio or a phase difference of an optimal RF shimming parameter obtained for each of a plurality of RF irradiation channels.

Therefore, the following relationships have been proved as a result of analyzing a relationship among optimal RF shimming parameters obtained for a plurality of respective RF irradiation channels. First, a B1 map is measured in advance for a plurality of different objects. An object may be a human body model, but, in the present example, a description will be made of an example using a B1 map obtained for a plurality of real objects.

Optimal RF shimming parameters are computed according to optimization computation disclosed in, for example, PTL 1, by using the B1 map measured for a plurality of different objects. The RF shimming parameters obtained through the computation are complex numbers which are obtained for a plurality of respective RF irradiation channels (for example, four channels). The following relationship has been found as a result of analyzing a relationship among principal components of the plurality of RF shimming parameters.

Figure 3:
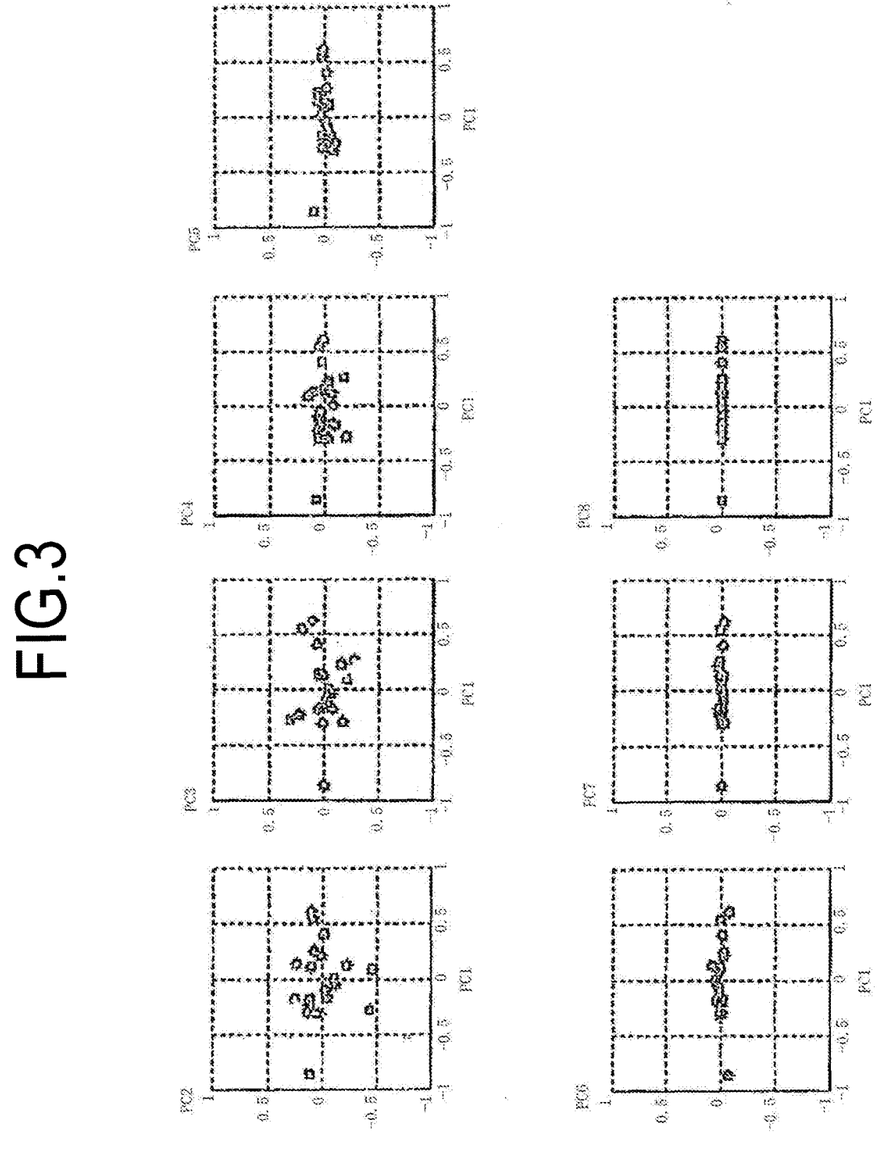
FIG. 3 is a diagram illustrating results of analyzing principal components of RF shimming parameters obtained through optimization computation by using a B1 map of heads of a plurality of persons acquired by using a plurality of irradiation channels.

FIG. 3 illustrates results of performing principal component analysis on RF shimming parameters which are obtained through optimization computation, by using a B1 map of the heads of nineteen persons, acquired by using four-channel RF irradiation coils. Here, in the present example, a description will be made of an example of a case where a plurality of RF irradiation channels are four-channel RF irradiation coils. In a case of the four-channel RF irradiation coils, since RF shimming parameters are expressed by four complex numbers, and each complex number has two components, a system of eight degrees of freedom is obtained. In the respective figures of FIG. 3, transverse axes express a value of a principal component PC1, and longitudinal axes express values of remaining principal components PC2 to PC8. As can be seen from the figures, the principal components PC4 to PC8 have the substantially same values regardless of objects.

Figure 4:
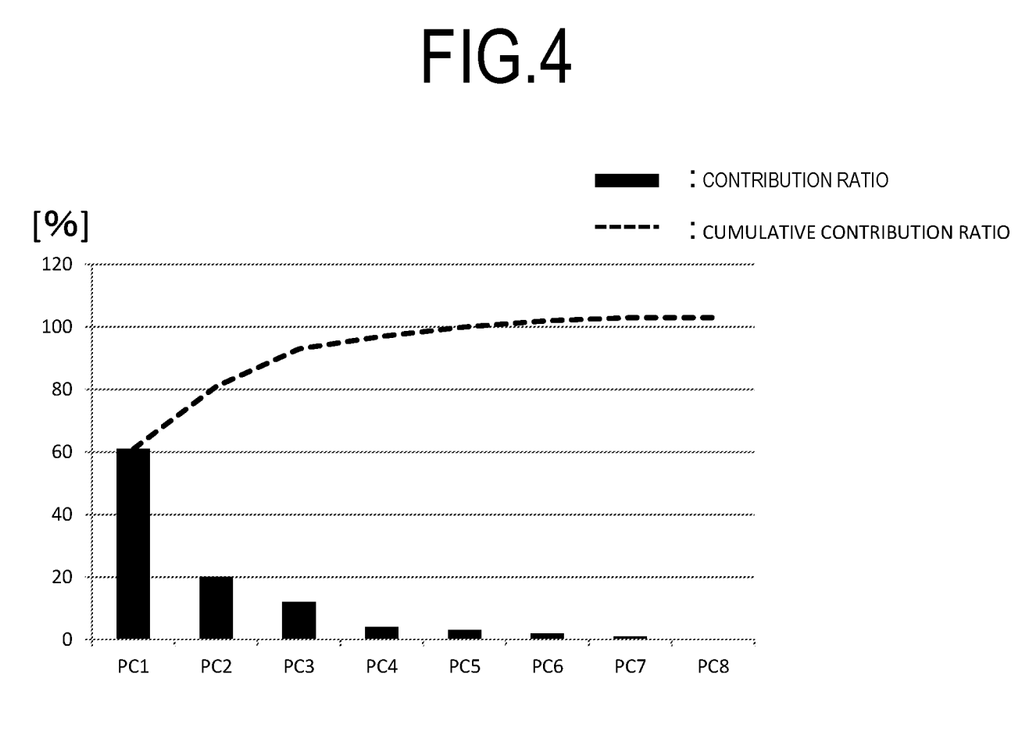
FIG. 4 is a diagram illustrating a contribution ratio and a cumulative contribution ratio of the principal components of the RF shimming parameters, which are analyzed.

FIG. 4 illustrates contribution ratios and a cumulative contribution ratio of principal components, which are analyzed. In FIG. 4, a transverse axis expresses the principal components PC1 to PC8, and a longitudinal axis expresses a contribution ratio and a cumulative contribution ratio. Here, the contribution ratio is an index indicating to what extent a principal component expresses non-homogeneity of original data. In the examples illustrated in FIGS. 3 and 4, a contribution ratio of PC1 is highest, and contribution ratios are high in the order of PC2 and PC3. In other words, the value of PC1 indicates large non-homogeneity, and the non-homogeneity is reduced in the order of the values of PC2 and PC3.

In other words, it can be seen that, in relation to B1 non-homogeneity, 90% or more of data of nineteen persons can be described with the principal components PC1 to PC3. Conversely, it can be said that, even if principal components whose contribution ratios are less than a set threshold value (for example, 10% to 15%) are set to a set value such as an average value of all objects, this has the small influence on optimization computation in RF shimming.

On the basis of these findings, the present example is characterized in that principal components whose contribution ratios are less than a set threshold value are constrained to a set value, and thus an RF shimming parameter capable of reducing a local SAR and a whole body SAR. Specifically, with respect to the principal components PC4 to PC8, a constraint condition A of fixing the principal components to the set value is imposed on RF shimming parameters. The set value in the constraint condition A may be, for example, an average value of pieces of data of the principal components PC4 to PC8 corresponding to nineteen persons, but is not limited thereto.

Figure 5:
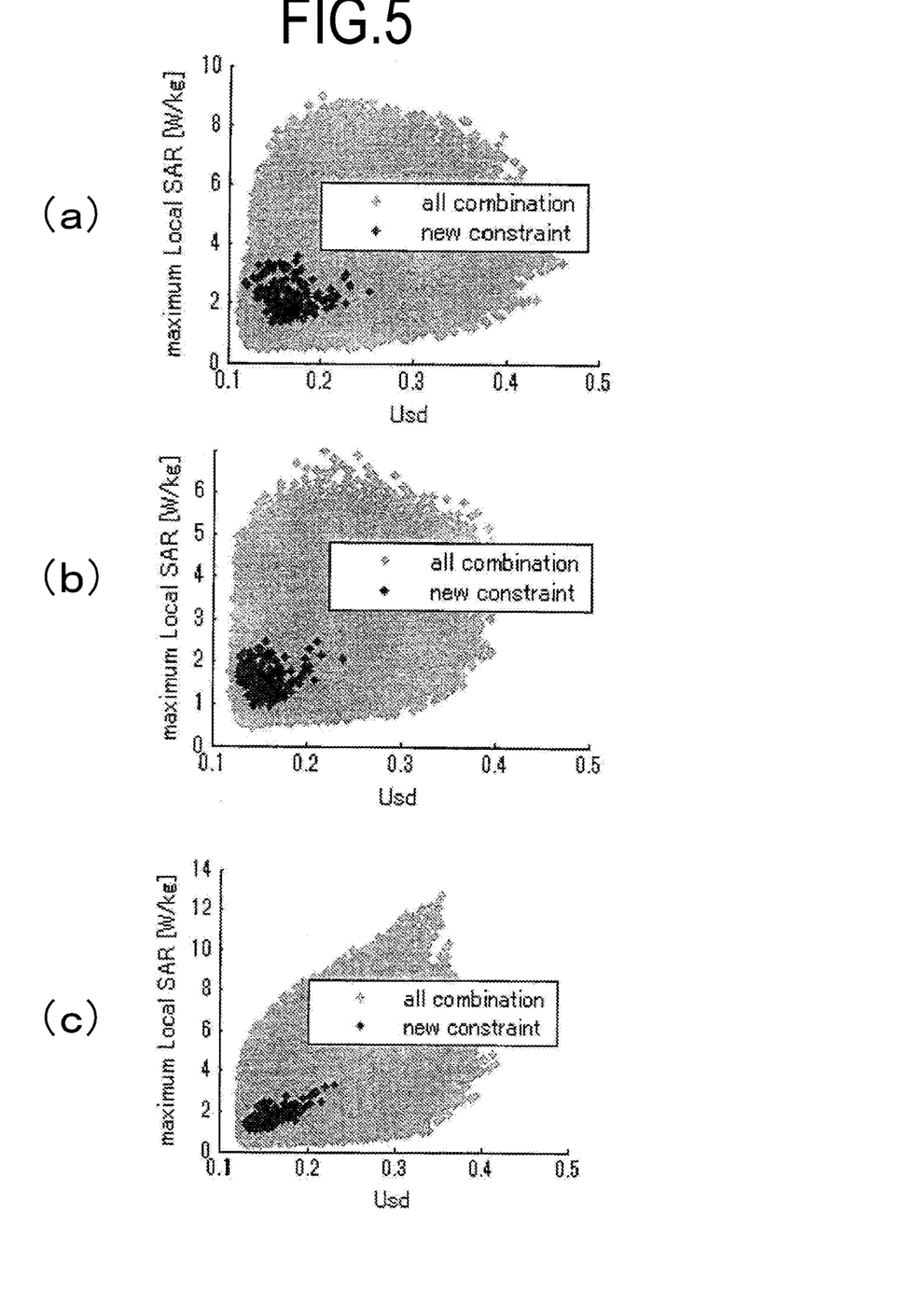
FIG. 5 is a diagram illustrating results of computing a local SAR according to a B1 map which is obtained by controlling RF irradiation coils with RF shimming parameters to which a constraint condition A is applied.

For checking, a local SAR was computed according to a B1 map which is obtained by controlling the RF irradiation coils with RF shimming parameters to which the constraint condition A is applied, by using a human body model. FIG. 5 illustrates a result thereof. In FIG. 5, a longitudinal axis expresses the maximum value of a local SAR, and a transverse axis expresses Usd which is an index of homogeneity, and FIG. 5 is a diagram in which computed values (local SAR maximum values) are plotted.

In local SAR computation, a local SAR was comprehensively computed by adjusting an RF shimming parameter in steps of an amplitude ratio of 2 dB and a phase difference of 20° within a preset variable range. FIGS. 5(a) to 5(c) illustrate different human body models M1 to M3. In the figures, computed values of all combinations are indicated by points (all combination) with low density, and computed values in which the principal components PC4 to PC8 are constrained to an average value are indicated by dark points (new constraint). It can be seen from these figures that the local SAR maximum value is reduced from 12.7 W/kg to 3.6 W/kg.

In other words, both of the local SAR maximum value and the homogeneity index Usd are improved, and thus the RF irradiation homogeneity is improved.

Steps S201 to S204 in FIG. 2 show process procedures of imposing a constraint condition on an RF shimming parameter capable of improving B1 non-homogeneity while reducing a local SAR on the basis of the above-described findings. In other words, in step S201, a B1 map group is read from a database in which B1 maps of a plurality of different imaging targets are accumulated.

Next, in step S202, the well-known optimization computation disclosed in PTL 1 or the like is performed by using each B1 map of the B1 map group, and an optimal RF shimming parameter is calculated for each B1 map.

In step S203, a relationship among a plurality of principal components PC corresponding to the number of irradiation channels is analyzed with respect to a parameter group of the obtained optimal RF shimming parameters. Through the analysis, principal components PC whose contribution ratios to a reduction of a local SAR are less than a threshold value are extracted.

In step S204, RF shimming parameters in which the extracted principal components are constrained to a set value are accumulated in the database in correlation with a plurality of respective different imaging targets. Here, the database may be built in an external storage device such as the magnetic disk 18.

Figure 6:
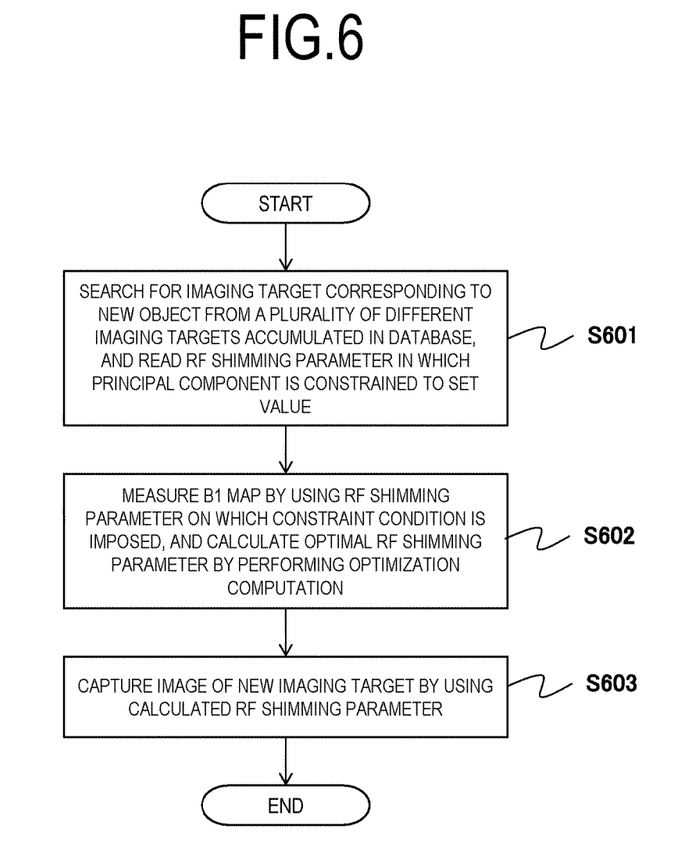
FIG. 6 is a flowchart illustrating procedures of performing imaging in which a local SAR is reduced, and B1 non-homogeneity is improved, by using RF shimming parameters on which a constraint condition of the present invention is imposed.

With reference to a flowchart of FIG. 6, a description will be made of a process of determining an RF shimming parameter of each RF irradiation channel for performing irradiation on a new imaging target (object) on the basis of the RF shimming parameters which are accumulated in the database and on which the constraint condition is imposed in the above-described way.

First, in step S601, an imaging target corresponding to a new object is searched for from a plurality of different imaging targets accumulated in the database, and an RF shimming parameter in which a principal component is constrained to a set value is read.

Nest, in step S602, a B1 map is measured by using the read RF shimming parameter on which the constraint condition is imposed, and an optimal RF shimming parameter is calculated by performing optimization computation.

In step S603, an RF shimming parameter calculated according to the RF shimming parameter on which the constraint condition is imposed is determined to be used for imaging, and the new object is imaged. Consequently, it is possible to capture an MR image of the new object in which a local SAR is reduced, and B1 non-homogeneity is also improved.

Example 2

Next, Example 2 will be described. The present example is different from Example 1 in that results of analyzing a plurality of principal components of RF shimming parameters are accumulated in a database.

Typically, an RF shimming parameter changes depending on an imaging part of an object or an objective function related to optimization computation even if the same object is imaged. Therefore, Example 2 is characterized in that an RF shimming parameter corresponding to an imaging part or an objective function is calculated, principal component analysis is performed on the calculated RF shimming parameter, and a plurality of constraint conditions corresponding to the imaging part or the objective function are accumulated in the database.

In the same manner as in the procedures in the flowchart illustrated in FIG. 2, first, B1 maps of a plurality of objects are respectively acquired for a plurality of imaging parts (for example, a slice position, the head, and the abdomen) in advance. Next, optimization computation of RF shimming is performed according to a plurality of different objective functions (for example, irradiation homogeneity, and a whole body SAR constraint) by using a B1 map of each object and each imaging part.

Principal component analysis is performed on RF shimming parameters obtained in the above-described way for each object, each imaging part, and each objective function. Constraint conditions with principal components whose contribution ratios to a reduction of a local SAR or the like are low as, for example, average values are determined, and are accumulated in the database in correlation with objects, imaging parts, and objective functions.

According to the present example, RF shimming parameters on which constraint conditions are imposed for each object, each imaging part, and each objective function are accumulated in the database. Therefore, when a new object is imaged, an RF shimming parameter on which a constraint condition corresponding to the object, an imaging part, and an objective function is read, optimization computation of RF shimming is performed, and thus it is possible to capture an MR image of the new object in which B1 non-homogeneity is improved while reducing a local SAR.

Example 3

Next, Example 3 will be described. The present example is different from Examples 1 and 2 in that a B1 map used for principal component analysis on an RF shimming parameter, and the RF shimming parameter are sequentially added to a database. In other words, when RF shimming is performed, a B1 map is necessarily acquired. Therefore, whenever a B1 map is acquired, the B1 map is accumulated in the database, and thus an amount of data used for principal component analysis on an RF shimming parameter is increased. Therefore, the accuracy or reliability of the principal component analysis is improved.

Specifically, an RF shimming parameter is computed by using an acquired new B1 map without imposing a constraint condition thereto. The computed new RF shimming parameter is added to RF shimming parameters already accumulated in the database, principal component analysis is performed thereon, and a new constraint condition is computed. A local SAR is computed again under the computed constraint condition. Data of one or a plurality of human body models, already accumulated in the database, is used for local SAR computation. In a case where the maximum value of the local SAR is smaller than the maximum value of the local SAR which is computed under the constraint conditions of the RF shimming parameters already accumulated in the database, the new constraint condition is accumulated in the database.

Consequently, according to the present example, since an amount of data which can be used for principal component analysis on an RF shimming parameter is increased, the accuracy or reliability of the principal component analysis is improved, and a local SAR can be further reduced.

Example 4

Next, Example 4 will be described. The present example is different from Examples 1 to 3 in that different constraint conditions are used for an RF shimming parameter depending on the age, the sex, a height, a weight, and the like of an object. In other words, a B1 map greatly depends on the physique of an object. Thus, an optimal constraint condition for an RF shimming parameter differs depending on the physique of an object. Therefore, the present example is characterized in that B1 maps are classified according to the age, the sex, a height, and a weight of each of objects in advance, principal component analysis is performed on an RF shimming parameter by using each B1 map so as to calculate a constraint condition, and the constraint condition is accumulated in a database in correlation with the age, the sex, the height, and the weight of the object. Consequently, since a constraint condition to be used is changed depending on the age, the sex, a height, and a weight of a new object to be examined, and then RF shimming can be performed, it is possible to improve an effect of the RF shimming.

As mentioned above, the present invention has been described on the basis of Examples 1 to 4, but the present invention is not limited thereto, it is obvious to a person skilled in the art that modifications or alterations may occur within the scope of the present invention, and the modifications or alterations are naturally included in the claims of the present application.

For example, in Examples 1 to 4, a description has been made of a case where B1 map data, a constraint condition imposed on an RF shimming parameter, and the like are accumulated in the database in correlation with, for example, the age, the sex, a height, a weight, and an imaging part of an object, and each objective function in RF shimming. This indicates that, since a constraint condition imposed on an RF shimming parameter related to improvement of a local SAR or magnetic field non-homogeneity is changed depending on an attribute of an object and an attribute of RF shimming, a constraint condition imposed on an RF shimming parameter is accumulated in the database in correlation with the attribute. Consequently, it is possible to improve B1 non-homogeneity while reducing a local SAR in an MRI apparatus including a plurality of RF irradiation channels.

REFERENCE SIGNS LIST

1 OBJECT, 2 STATIC MAGNETIC FIELD GENERATION SYSTEM, 3 GRADIENT MAGNETIC FIELD GEN-

ERATION SYSTEM, 4 SEQUENCER, 5 SIGNAL TRANSMISSION SYSTEM, 6 SIGNAL RECEPTION SYSTEM, 7 SIGNAL PROCESSING SYSTEM, 8 CENTRAL PROCESSING UNIT (CPU), 9 GRADIENT MAGNETIC FIELD COIL, 10 GRADIENT MAGNETIC FIELD POWER SOURCE, 11 HIGH FREQUENCY OSCILLATOR, 12 MODULATOR, 13 HIGH FREQUENCY AMPLIFIER, 14a HIGH FREQUENCY COIL (TRANSMISSION COIL), 14b HIGH FREQUENCY COIL (RECEPTION COIL), 15 SIGNAL AMPLIFIER, 16 QUADRATURE PHASE DETECTOR, 17 A/D CONVERTER, 18 MAGNETIC DISK, 19 OPTICAL DISC, 20 DISPLAY, 23 TRACK BALL OR MOUSE, 24 KEYBOARD, 51 GANTRY, 52 TABLE, 53 CASING, 54 PROCESSING DEVICE

The invention claimed is:

1. A magnetic resonance imaging apparatus comprising:
a control calculation unit that controls each of a plurality of irradiation channels on the basis of RF shimming parameters corresponding to the plurality of irradiation channels, and performs imaging sequence of irradiating an object with an RF magnetic field, wherein the control calculation unit imposes a constraint condition on at least one of a plurality of principal components obtained through principal component analysis on the RF shimming parameters, so as to obtain the RF shimming parameters;
a first database in which the RF shimming parameters for respectively controlling the plurality of irradiation channels are stored; and
a second database in which B1 maps of a plurality of different imaging targets are accumulated,
wherein the control calculation unit
reads a B1 map group from the second database,
performs optimization computation of RF shimming by using each B1 map of the read B1 map group,
extracts principal components whose contribution ratios to a reduction of a local SAR are less than a threshold value from a plurality of principal components corresponding to the number of irradiation channels, obtained by using a parameter group of the obtained optimal RF shimming parameters, and
accumulates RF shimming parameters obtained by constraining the extracted principal components to a set value in the first database in correlation with the plurality of respective imaging targets.

2. The magnetic resonance imaging apparatus according to claim 1,
wherein the constraint condition imposed on the RF shimming parameters is accumulated in the first database in correlation with an attribute of the object and an attribute of RF shimming.

3. The magnetic resonance imaging apparatus according to claim 2,
wherein the attribute is at least one of the age, the sex, a height, a weight, and an imaging part of the object, and an objective function in RF shimming.

4. A method performed by a magnetic resonance imaging apparatus, for setting RF shimming parameters for controlling each of a plurality of irradiation channels irradiating an object with RF magnetic fields,
the magnetic resonance imaging apparatus comprising:
a control calculation unit that controls each of the plurality of irradiation channels on the basis of the RF shimming parameters corresponding to the plurality of irradiation channels, and performs imaging sequence of irradiating the object with an RF magnetic field;
a first database in which the RF shimming parameters for respectively controlling the plurality of irradiation channels are stored; and
a second database in which B1 maps of a plurality of different imaging targets are accumulated,
the method comprising:
obtaining the RF shimming parameters by imposing a constraint condition on at least one of a plurality of principal components obtained through principal component analysis on the RF shimming parameters, including
reading a B1 map group from the second database,
performing optimization computation of RF shimming by using each B1 map of the read B1 map group,
extracting principal components whose contribution ratios to a reduction of a local SAR are less than a threshold value from a plurality of principal components corresponding to the number of irradiation channels, obtained by using a parameter group of the obtained optimal RF shimming parameters, and
accumulating RF shimming parameters obtained by constraining the extracted principal components to a set value in the first database in correlation with the plurality of respective imaging targets.

* * * * *